(12) United States Patent
Albrecht et al.

(10) Patent No.: US 9,663,480 B2
(45) Date of Patent: May 30, 2017

(54) BIS-MMF DERIVATIVES

(71) Applicant: RATIOPHARM GMBH, Ulm (DE)

(72) Inventors: Wolfgang Albrecht, Ulm (DE); Roland Selig, Ulm (DE); Sebastian Rabe, Neu-Ulm (DE); Annemarie Maier, Biberach (DE); Richard Guserle, Kötz (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 15/037,669

(22) PCT Filed: Dec. 4, 2014

(86) PCT No.: PCT/EP2014/076524
§ 371 (c)(1),
(2) Date: May 18, 2016

(87) PCT Pub. No.: WO2015/082590
PCT Pub. Date: Jun. 11, 2015

(65) Prior Publication Data
US 2016/0289201 A1  Oct. 6, 2016

(30) Foreign Application Priority Data

Dec. 5, 2013 (EP) ..................... 13005665
Dec. 20, 2013 (EP) ..................... 13198729

(51) Int. Cl.
*C07D 295/088* (2006.01)

(52) U.S. Cl.
CPC ................. *C07D 295/088* (2013.01)

(58) Field of Classification Search
CPC .................................. C07D 295/088
See application file for complete search history.

(56) References Cited

FOREIGN PATENT DOCUMENTS

WO  WO 2013/175359  * 11/2013

OTHER PUBLICATIONS

PCT/EP2014/076524, Int'l Preliminary Report on Patentability & Written Opinion of the ISA, Jun. 7, 2016.
PCT/EP2014/076524, Int'l Search Report, Jun. 9, 2015.

* cited by examiner

*Primary Examiner* — Erich A Leeser
(74) *Attorney, Agent, or Firm* — Milstein Zhang & Wu LLC

(57) ABSTRACT

The present invention relates to novel compounds, e.g. for use as a medicament. In particular, the present invention relates to novel medicaments, preferably in the treatment and/or prevention of systemic diseases, autoimmune diseases, or inflammatory diseases, for example multiple sclerosis and psoriasis.

10 Claims, 1 Drawing Sheet

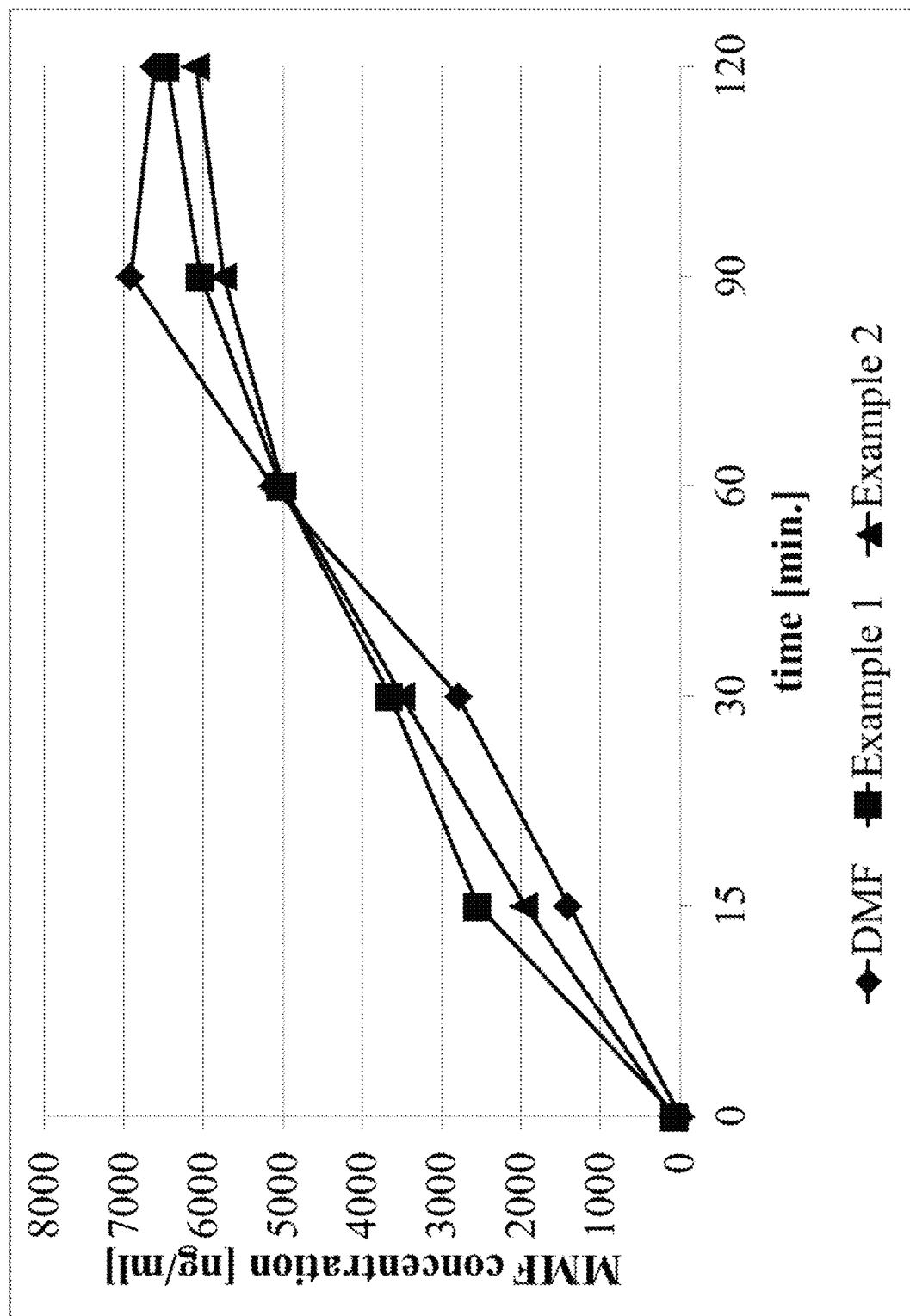

BIS-MMF DERIVATIVES

The present invention relates to novel compounds, preferably for use as a medicament. In particular, the present invention relates to novel prodrugs of monomethyl fumarate (MMF) suitable as a medicament, preferably in the treatment and/or prevention of systemic diseases, autoimmune diseases, and/or inflammatory diseases, for example multiple sclerosis and psoriasis. Further, the invention relates to a pharmaceutical composition comprising said compounds.

BACKGROUND OF THE INVENTION

Dimethyl fumarate (DMF) is an oral therapeutic agent which is reported to reduce the rejection often occurring in connection with organ transplantation (host versus graft reaction). Further, DMF is approved to be suitable as medicament for the treatment or prevention of a variety of diseases. For example, DMF is proposed in the treatment of autoimmune diseases such as multiple sclerosis. Further, DMF is suggested to be a suitable active pharmaceutical agent in the treatment of psoriasis.

DMF is characterized by the following chemical Formula (1):

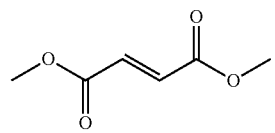

Formula (1)

When taken orally DMF is reported to be hydrolyzed for example by the acidic ambience of the stomach or by esterases in the intestine to monomethyl fumarate (MMF). MMF can be regarded as a metabolite of DMF and can be characterized by the following chemical Formula (2):

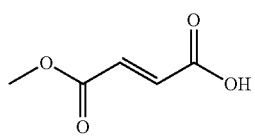

Formula (2)

The mechanism of action of DMF or its metabolite MMF is reported to include inhibition of cytokine-induced nuclear translocation of the nuclear factor kappa B (NF-κB), apoptosis of stimulated T cells, and increased production of the $T_h2$ cytokines IL-4 and IL-5 in stimulated T cells, whereas generation of the $T_h1$ cytokine interferon gamma (IFN-γ) is supposed to remain unaffected. DMF is described to activate the transcription factor Nrf2 (nuclear factor erythroid 2-related factor 2), which binds to antioxidant response elements in the promoters of protective genes such as NADPH-quinone-oxidoreductase-1 (NQO1) and heme-oxygenase-1. Thus, this ultimately raises the levels of the important intracellular antioxidant glutathione (cf. Albrecht P. et al., Journal of Neuroinflammation 2012, 9:163).

Further, it is alleged that the treatment of animals or primary cultures of CNS cells with DMF or MMF resulted in increased nuclear levels of active Nrf2, with subsequent up-regulation of canonical antioxidant target genes. DMF or MMF treatment increased cellular redox potential, glutathione, ATP levels, and mitochondrial membrane potential in a concentration-dependent manner. Treating astrocytes or neurons with DMF or MMF also significantly improved cell viability after toxic oxidative challenge in a concentration-dependent manner. This effect on viability was lost in cells that had eliminated or reduced Nrf2. These data suggest that DMF and MMF are cytoprotective for neurons and astrocytes against oxidative stress-induced cellular injury and loss, potentially via up-regulation of an Nrf2-dependent antioxidant response. Thus, in summary, it is indicated that in vivo DMF and MMF show about the same efficacy, in particular on the transcription factor Nrf2.

However, the commercial use of DMF is restricted due to several reasons.

Further it is reported that DMF has to be administered in quite high amounts and that the pharmaceutically active agent often shows undesirable side effects such as flush and especially symptoms related to the gastrointestinal tract such irritation of the stomach and diarrhoea.

Consequently, there is a need for new compounds being bioequivalent to DMF (or showing a similar dissociation under respective in-vitro conditions), preferably for use as a medicament, more preferably in the treatment and/or prevention of systemic diseases, autoimmune diseases, and/or inflammatory diseases, for example multiple sclerosis and psoriasis. Further, said medicaments should be capable of being applied in appropriate doses and should not cause significant undesired side effects.

It was an object of the present invention to provide compounds to be used as a medicament for the above-mentioned diseases, wherein said compounds show bioequivalent pharmacokinetic properties compared to DMF.

Moreover, compounds should be provided which are hydrolyzed within the intestine with substantially the same rate of hydrolysis as DMF (or under respective in-vitro conditions).

Further, the compound should preferably cause little undesirable side effects.

More over, the compound should show a similar permeation behaviour compared to the one of DMF.

Additionally, it was an object of the present invention to provide compounds which can be used in the treatment of the early phase of an autoimmune disease, in particular of multiple sclerosis.

SUMMARY OF THE INVENTION

According to the present invention, the above objectives are achieved by the specific compounds described herein by Formula (I). Said compounds can be used as a medicament for the treatment and/or prevention of systemic diseases, autoimmune diseases, and/or inflammatory diseases, for example multiple sclerosis and psoriasis.

The compounds of the present invention can be regarded as prodrugs. Generally, a prodrug can be regarded as a substance that is administered to a subject (preferably human) in a pharmacologically inactive or pharmacologically less than fully active form, and is subsequently converted in the body of the subject to an active drug, preferably through metabolic processes occurring in the body of the subject. In other words, a prodrug usually serves as a type of 'precursor' to the intended drug.

Thus, the subject of the present invention are compounds according to the following Formula (I):

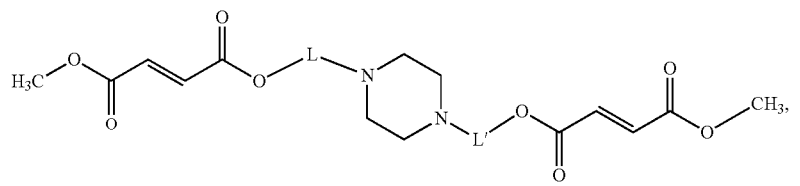

Formula (I)

wherein L and L' are each an alkanediyl residue with 1 to 6 carbon atoms, alternatively 2 to 6 carbon atoms.

It was found that the compounds according to Formula (I) of the present invention show excellent pharmaceutical and/or pharmacokinetic properties. In particular, the compounds show the desired hydrolysis rate being substantially the same as the one of DMF.

Another subject of the invention is a compound according to Formula (I) for use as a medicament.

Further, the present invention relates to a compound according to Formula (I) for use in the treatment and/or prevention of systemic diseases, autoimmune diseases, and/or inflammatory diseases, preferably for use in the treatment of multiple sclerosis or psoriasis, in particular multiple sclerosis.

Another subject is a pharmaceutical composition comprising the above-mentioned compound according to Formula (I).

Another subject of the present invention is the process of producing a compound according to the present invention by reacting an activated form of monomethyl fumarate with a substance comprising two hydroxy groups.

BRIEF DESCRIPTION OF THE DRAWINGS

FIG. 1 shows incubation experiments with DMF (reference) and compounds of the invention.

DETAILED DESCRIPTION OF THE INVENTION

In the context of this invention, the compound of the present invention is represented by the above Formula (I). Further, in the present invention the compound according to Formula (I) also refers to its polymorphs, stereoisomers, solvates or hydrates, as well as pharmaceutically acceptable salts and mixtures thereof.

The compound according to Formula (I) can preferably comprise the pharmaceutically acceptable acid addition salts of the inventive compound. The acids which are used to prepare the pharmaceutically acceptable acid addition salts are preferably those which form non-toxic acid addition salts, i.e. salts containing pharmacologically acceptable anions, such as chloride, bromide, iodide, nitrate, sulfate, bisulfate, phosphate, acid phosphate, acetate, lactate, citrate, tartrate, (D,L)- and L-malate, bitartrate, succinate, maleate, fumarate, gluconate, saccharate, benzoate, ascorbat, tosylate, mesilate, besilate, aspartate, D-gluconate, glycolate. A preferred salt is the dihydrochloride of a compound according to Formula (I).

In a particularly preferred embodiment of the present invention a single compound according to Formula (I) can be used as medicament.

The same can be applied to the pharmaceutical composition comprising the compound according to Formula (I).

L and L' are each independently an alkanediyl residue with 1 to 6 carbon atoms or alternatively 2 to 6 carbon atoms.

Alkanediyl residues comprise linear and branched alkanediyl residues. Examples for alkanediyl residues are for example —CH$_2$—, —(CH$_2$)$_2$—, —CH(CH$_3$)—, —(CH$_2$)$_3$—, —CH$_2$CH(CH$_3$)—, —CH(CH$_3$)CH$_2$—, —CH(C$_2$H$_5$)—, —C(CH$_3$)$_2$—, —(CH$_2$)$_4$—, —(CH$_2$)$_2$CH(CH$_3$)—, —CH$_2$CH(CH$_3$)CH$_2$—, —CH(CH$_3$)(CH$_2$)$_2$—, —CH(C$_2$H$_5$)CH$_2$—, —CH$_2$CH(C$_2$H$_5$)—, —C(CH$_3$)$_2$CH$_2$—, —CH$_2$C(CH$_3$)$_2$—, —CH(CH$_3$)CH(CH$_3$), —CH(C$_3$H$_7$)—, —(CH$_2$)$_5$, —(CH$_2$)$_3$CH(CH$_3$), —(CH$_2$)$_2$CH(CH$_3$)CH$_2$—, —CH$_2$CHCH$_3$(CH$_2$)$_2$—, —CH$_2$C(CH$_3$)$_2$CH$_2$—, —(CH$_2$)$_2$C(CH$_3$)$_2$—, —(CH$_2$)$_6$—, —(CH$_2$)$_4$CH(CH$_3$)—, —(CH$_2$)$_3$CH(CH$_3$)CH$_2$—, —CH$_2$CHCH$_3$(CH$_2$)$_3$—, —(CH$_2$)$_3$C(CH$_3$)$_2$— and —(CH$_2$)$_2$C(CH$_3$)$_2$CH$_2$—

In preferred embodiment L and L' can be the same alkanediyl residue. Compounds having the same linker can preferably be prepared in an easier and more economic way.

It is further preferred that L as well as L' are independently linear alkanediyl residues with 2 to 6 carbons atoms, preferably with 2, 3 or 4 carbon atoms, more preferably with 2 or 4 carbon atoms, in particular with 2 carbons atoms.

It is more preferred that L and L' are both linear alkanediyl residues with 1 to 6 carbons atoms, preferably with 2, 3 or 4 carbon atoms.

In a preferred embodiment the inventive compound is represented by the following Formula (Ia)

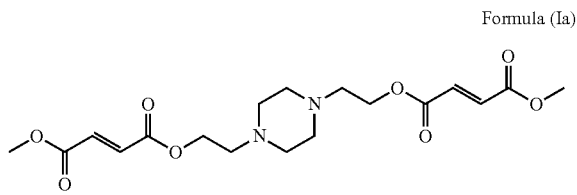

Formula (Ia)

In Formula (Ia) L and L' are —(CH$_2$)$_2$—.

A compound according to Formula (I) can preferably be synthesized via the following route:

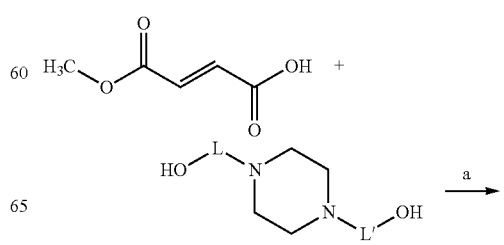

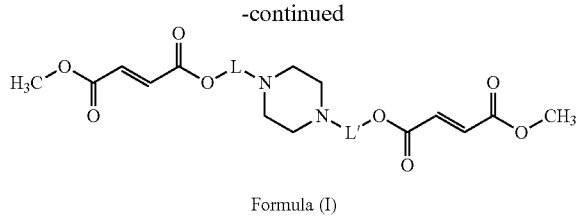

Formula (I)

Preferably, in step a, MMF and the bis (hydroxylalkyl) piperazine derivative can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Coupling agents are reported to be used in case that one or both of the educts further bear a group being labile in acidic or alkaline milieu, since the reaction is carried out under neutral conditions. Suitable coupling agents can be for example DCC (N,N'-dicyclohexylcarbodiimide), DIC (N,N'-diisopropylcarbodiimide), EDC (N-ethyl-N'-(3-methylaminopropyl)carbodiimide hydrochloride), CDI (carbonyldiimidazole), preferably EDC in combination with DMAP (4-(dimethylamino)pyridine).

A suitable organic solvent can for example be dichloromethane, chloroform, dioxane, acetonitrile, tetrahydrofuran and dimethylformamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with a bis(hydroxyalkyl) piperazine derivative, preferably in an organic solvent, such as dioxane, tetrahydrofuran, chloroform or dichloromethane. Further, the reaction of the acid chloride with the bis(hydroxyalkyl) piperazine derivative is preferably carried out in the presence of an auxiliary alkaline compound. Suitable alkaline compounds are for example pyridine and amines, such triethylamine, and diisopropylethylamine, preferably triethylamine.

The compound according to Formula (I) shows excellent pharmacokinetic properties, wherein these properties are substantially bioequivalent to the ones of DMF. Within two hours the compounds show a hydrolysis into MMF wherein the hydrolysis is substantially the same as the one of DMF. As a result, the same amount of MMF is released within the two hours and thus the compounds can be referred to as compounds (prodrugs of MMF) with substantially the same enhanced release of MMF. Additionally, the remaining organic residue is not expected to harm the patient's organism.

Further, the present invention relates to the compounds according to Formula (I) for use as a medicament.

A further subject of the invention is the inventive compound for use in the treatment and/or prevention of systemic diseases, autoimmune diseases and/or inflammatory diseases.

Systemic diseases do not just affect single organs. Instead, these diseases are known to affect a number of organs and tissues or even the body as a whole.

People having an autoimmune disease usually suffer from their immune system mistakenly attacking their own cells of their organism and thus incorrectly responding to substances normally present in the body.

An inflammation can be defined as the response of the body to the occurrence of harmful stimuli which can result in pain, heat, redness, swelling and loss of function of the affected organ.

It is possible that some of the above-mentioned diseases cannot be allocated in one single group of the above-mentioned groups, since they show the symptoms of more than one of them.

In a further preferred embodiment the inventive compound is for use in the treatment of multiple sclerosis and psoriasis, preferably multiple sclerosis. The compound of the present invention can e.g. be used in the treatment of the following types of multiple sclerosis, relapsing-remitting, primary-progressive, secondary-progressive, and progressive-relapsing. In a preferred embodiment the compound of the present invention are used in the treatment of relapsing-remitting multiple sclerosis.

Further, the present invention also provides a pharmaceutical composition comprising the compounds according to the present invention, i.e. a pharmaceutical composition comprising a prodrug of MMF according to Formula (I) and optionally pharmaceutical excipients.

In a preferred embodiment the pharmaceutical composition comprises
(i) 0.01 to 10 mmol, more preferably 0.05 to 5 mmol, still more preferably 0.25 to 3.5 mmol and particularly preferred 0.5 to 2.5 mmol of a compound according to the present invention;
(ii) pharmaceutical excipient(s).

In a further preferred embodiment the present composition can comprise one or more further excipients, preferably pharmaceutical excipients as described in the European Pharmacopoeia (Ph. Eur.) and/or in the US Pharmacopoeia (USP).

Examples of pharmaceutical excipients are carriers, binders, fillers, disintegrants, wicking agents, glidants and/or lubricants.

In a preferred embodiment the excipients are chosen such that the resulting formulation is a gastric juice-resistant formulation. In a preferred embodiment the formulation of the present invention does not show significant drug release under acidic conditions. In particular, the in-vitro drug release after 2 hours is less than 10%, preferably 0 to 9.9%, more preferably 0 to 5%, still more preferably 0.001 to 3%, measured according to USP, Apparatus II, paddle, 0.1N HCl, 37° C., 50 rpm.

The pharmaceutical composition can be in a form suitable for oral administration, preferably in the form of a tablet or capsule, in particular in form of a tablet.

It is further preferred that the tablet is coated with a film coating. Alternatively, the capsule can also be coated.

In the present invention, the following three types of film coatings are possible:
film coating without affecting the release of the active ingredient,
gastric juice-resistant film coatings,
retard film coatings.

Generally, film coatings can be prepared by using film-forming agents such as waxes, cellulose derivatives, poly (meth)acrylate, polyvinylpyrrolidone, polyvinyl acetate phthalate, and/or shellac or natural rubbers such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating being stable in the pH range of about 0.7 to 3.0, which is supposed to be the pH-value of human gastric juice found in the stomach. However, in an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents being for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxypropyl methyl cellulose phthalate, hydroxypropyl methyl cellulose acetate succinate, cellulose acetate trimellitat, and meth(acrylic)acid copolymers such as methyl acrylate-methacrylic acid copolymers, methyl methacrylate-methacrylic acid copolymers, Eudragits (for example Eudragit® L30D, Eudragit® L, Eudragit® S).

The coating is preferably free of active ingredient. It is further preferred that the thickness of the coating is usually 10 µm to 2 mm, preferably from 50 to 500 µm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

In a preferred embodiment the pharmaceutical composition can be administered one to three times a day, preferably once or twice a day, more preferably once a day.

Further, the present invention relates to a method for treating and/or preventing systemic diseases, autoimmune diseases and/or inflammatory diseases, preferably multiple sclerosis or psoriasis, in particular multiple sclerosis, comprising administering to a subject in need thereof a therapeutically effective amount of the compound of the invention or the pharmaceutical composition of the invention. For the compound and the pharmaceutical composition administered in the before-mentioned method the same applies as to the compound and the pharmaceutical composition as described above in the text, respectively.

The invention is illustrated by the following examples.

EXAMPLES

Example 1

(E)-But-2-enedioic acid-2-{4-[2-((E)-3-methoxycarbonyl -acryloyloxy)-ethyl]-piperazin-1-yl}-ethyl ester methyl ester

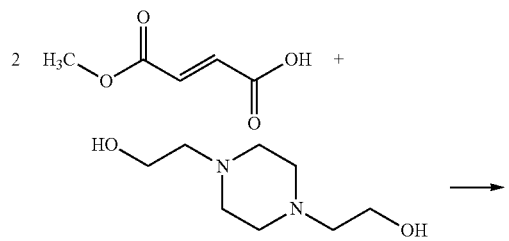

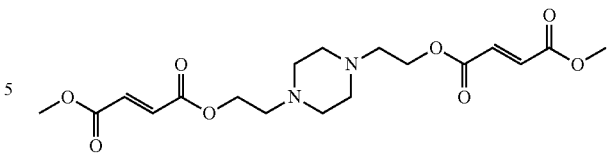

To a stirred suspension of monomethyl fumarate (1.64 g; 12.6 mmol) in dry dichloromethane (30 mL) were added successively N-ethyl-N'-(3-methylaminopropyl)carbodiimide hydrochloride (2.4 g; 12.6 mmol), 1,4-bis(2-hydroxyethyl) piperazine (1 g; 5.7 mmol) and DMAP (70 mg; 0.6 mmol) at 0° C. The suspension was allowed to warm to room temperature (23° C.) and stirring was continued overnight (for 14 hours). The mixture was diluted with additional dichloromethane (50 mL), washed with water (2×70 mL) and dried over sodium sulfate. After the removal of the solvent the resulting crude product was purified via silicagel chromatography (eluent: ethyl acetate/triethylamine 99:1).

Yield: 970 mg (2.4 mmol; 42%)

Example 2

(E)-But-2-enedioic acid-2-{4-[2-((E)-3-methoxycarbonyl -acryloyloxy)-ethyl]-piperazin-1-yl}-ethyl ester methyl ester dihydrochloride

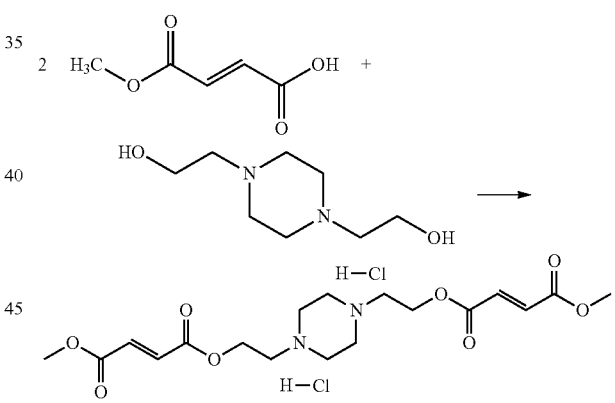

To a stirred suspension of monomethyl fumarate (1.64 g; 12.6 mmol) in dry dichloromethane (30 mL) were added successively N-ethyl-N'-(3-methylaminopropyl)carbodiimide hydrochloride (2.4 g; 12.6 mmol), 1,4-bis(2-hydroxyethyl) piperazine (1 g; 5.7 mmol) and DMAP (70 mg; 0.6 mmol) at 0° C. The suspension was allowed to warm to room temperature (23° C.) and stirring was continued overnight (for 14 hours). The mixture was diluted with additional dichloromethane (50 mL), washed with water (2×70 mL) and dried with sodium sulphate. After the removal of the solvent the resulting crude product was purified via silicagel chromatography (eluent: ethylacetate/triethylamine 99:1). The resulting substance was dissolved in dichloromethane and HCl (3M in BuOH; 4 eq.) was added. The precipitated product was collected via filtration.

Yield: 1.14 g (2.4 mmol; 42%)

Example 3

Investigation and Comparision of the Kinetics of MMF-Release of the Different Compounds of the Present Invention and DMF During Incubation in Intestinal Fluid from the Minipig 1. Materials 1.1. Test Compounds Compounds of the present invention were synthesized as described above.

1.2. Intestinal Fluid

Intestinal fluid samples were prepared at CiToxLAB Scantox A/S. The samples were taken from 1 female Gottingen SPF minipig from CiToxLAB Scantox A/S standard stock, originally obtained from Ellegaard Gottingen Minipigs A/S, DK-4261 Dalmose, Denmark. The minipig was 10 months old and the body weight was 21 kg. The minipig was identified by an individual number tagged to the pinna of one ear (animal number is documented in the raw data).

The minipig was fasted for approximately 28 hours before sampling of intestinal fluid. On the day of sampling, the minipig was weighed and anaesthetised by an intramuscular injection in the neck or in the left hind leg (about 0.3 ml per kg body weight) of a mixture of Zoletil 50 Vet., Virbac, France (125 mg tiletamine and 125 mg zolazepam), Rompun Vet., Bayer, Germany (20 mg xylazine/ml, 6.5 ml), Ketaminol Vet., Veterinaria AG, Switzerland (100 mg ketamine/ml, 1.5 ml) and Methadon DAK, Nycomed Danmark, Denmark (10 mg methadon/ml, 2.5 ml).

Intestinal fluid was obtained by flushing one jejunal segment, measuring 30.2 cm, with saline. Intestinal fluid together with saline used for flushing was placed in centrifuge tubes. All samples were frozen at −70° C. and shipped on dry ice to the Sponsor for further use.

2. Analytical Methods 2.1. Quantification of MMF by LC-MS 2.1.1. Analytical Instrument

| | |
|---|---|
| Instrument: | Acquity UPLC system coupled with a TQ detector (triple quadruple mass spectrometer) |
| UPLC method: | |
| Column: | Phenomenex Kinetex C18, 100 A, 2.6 μm (150 × 4.6 mm) |
| flow: | 0.4 ml/min |
| split: | appr. 100 μl/min to MS |
| Temperature: | 30° C. |
| solvet system (isocratic): | |
| Solvent A | 25% water with 0.1% acetic acid |
| Solvent B | 75% methanol with 0.1% acetic acid |
| stoptime: | 6 min |
| autosampler temperature: | 8° C. |
| injection volume: | 4 μl |
| retention time: | MMF: 4.3 min |
| | MEF: 4.7 min |
| Mass spectrometry | |
| software: | Masslynx 4.1 |
| detection mode: | electrospray/negative ions (ESP−) |
| capillary voltage: | 2.3 kV |
| source temperature: | 100° C. |
| desolvation temperature: | 450° C. |
| cone voltage: | 18 V |
| desolvation gas: | $N_2$, 650 L/h |
| cone gas: | $N_2$, 20 L/h |
| collision gas: | argon, appr. $3.3 * 10^{-3}$ mbar |
| collision energy: | 11 eV |
| MRM [m/z]: | 128.94 > 85.03 Monomethylfumarate dwell: 200 msec |
| | 142.99 > 99.06 Monoethylfumarate (ISTD) dwell: 200 msec |

2.1.2. Stock and Calibration Solutions

Stock (SS), working (WS) and calibration solutions of the analyte monomethyl fumarate (MMF) and the internal standard (ISTD) monoethyl fumarate (MEF) were prepared as described below.

$SS_{MMF}$: In a 10 ml volumetric flask, 6.5 mg MMF (Batch: MKRJ0642V/Aldrich) were dissolved in methanol and made up to volume (c=650 μg/ml)

$SS_{ISTD}$: In a 100 ml volumetric flask, 10 mg MEF (Batch: STBC5219V/Aldrich) were dissolved in methanol and made up to volume (c=100 μg/ml)

$WS_{ISTD}$: 100 μl SSISTD were transferred into a 10 ml volumetric flask and made up to volume with acetonitrile (c=1,000 ng/ml);

Calibration solutions were prepared by serial dilution of $SS_{MMF}$; diluted small intestinal fluid (diluted by 1/20 v/v with 50 mM $KH_2PO_4$, pH 6.8; (dil IF) was used as matrix. The dilution scheme is given below:

| calibration solution | Preparation | Concentration [ng/ml] | [μM] |
|---|---|---|---|
| cal6500 | 8 μl $SS_{MMF}$ + 792 μl dil IF | 6500 | 50 |
| cal3250 | 50 μl cal6500 + 50 μl dil IF | 3250 | 25 |
| cal650 | 20 μl cal6500 + 180 μl dil IF | 650 | 5.0 |
| cal325 | 50 μl cal650 + 50 μl dil IF | 325 | 2.5 |
| cal65 | 10 μl cal650 + 90 μl dil IF | 65 | 0.5 |

2.1.3. Sample Preparation

50 μl sample (calibration solution or sample of an incubation experiment with MMF prodrugs) was mixed with 50 μl $WS_{ISTD}$, 20 μl formic acid and 100 μl acetonitrile. This mixture was vortexed for 15 sec and centrifuged (13,000 rpm, 3 min). Thereafter, 4 μl of the supernatant were subjected to LC-MS analysis.

2.2. Incubation Experiments with DMF (Reference) and Compounds of the Invention 2.2.1. Stock Solutions Stock solutions were prepared in DMSO or, for one compound, in DMSO with 10% (v/v) water. Concentrations in stock solutions were 5.00, 2.50 and 1.67 mmol for compounds with one, two and three molar MMF equivalents.

| Compound | MW | Sample weight [mg] | dissolved in | Concentration [mg/ml] | [mmol] |
|---|---|---|---|---|---|
| DMF | 144.13 | 7.21 | 10 ml DMSO | 0.721 | 5.00 |
| Example 1 | 398.42 | 4.98 | 5 ml DMSO | 0.996 | 2.50 |
| Example 2 | 471.34 | 5.89 | 5 ml DMSO + 10% $H_2O$ | 1.178 | 2.50 |

2.2.2. Incubation Experiment

In a HPLC glass vial, 8 μl of stock solution were mixed with 792 μl dil IF and the mixture was stirred (250 rpm) in a water bath (T=37° C.).

Immediately after mixing as well as at t=15 min, 30 min, 60 min, 90 min and 120 min, 50 μl were withdrawn and prepared for LC-MS analysis as described in chapter. 2.1.3.

Incubations were continued and in case the result of analysis of the 120 min indicated the presence of remaining intact MMF prodrug, additional samples were taken (t=360 or 420 min and at 1,260 or 1,320 min) and analysed.

3. Results 3.1. Calibration of the Analytical Method

Each calibration solution was analysed two-fold. The second analysis was carried out approx. 18 h after storage of the sample in the autosampler, which was cooled to 8° C. The results demonstrate that the ratio of peak area remains essentially unchanged between the first and the second analysis.

The concentration/peak area ratio data pairs were subjected to regression analysis with 1/x weighting and the resulting calibration equation was used to quantify the MMF content in incubation samples.

| calibration standard | nominal concentration [ng/ml] | Analysis | area/area(ISTD) | mean | RSD |
|---|---|---|---|---|---|
| cal6500 | 6,500 | 1st analysis | 3.569 | 3.567 | 0.07 |
|  |  | 2nd analysis | 3.564 |  |  |
| cal3250 | 3,250 | 1st analysis | 1.710 | 1.681 | 1.73 |
|  |  | 2nd analysis | 1.652 |  |  |
| cal650 | 650 | 1st analysis | 0.348 | 0.347 | 0.29 |
|  |  | 2nd analysis | 0.346 |  |  |
| cal325 | 325 | 1st analysis | 0.174 | 0.169 | 2.96 |
|  |  | 2nd analysis | 0.164 |  |  |
| cal65 | 65 | 1st analysis | 0.036 | 0.035 | 2.86 |
|  |  | 2nd analysis | 0.034 |  |  |
| cal0 | 0 | 1st analysis | 0.000 | 0.000 | 0.00 |
|  |  | 2nd analysis | 0.000 |  |  |

As can be seen from FIG. 1 the inventive compounds according to Example 1 and 2 show substantially the same hydrolysis to MMF than DMF.

The invention claimed is:

1. Compound according to Formula (I)

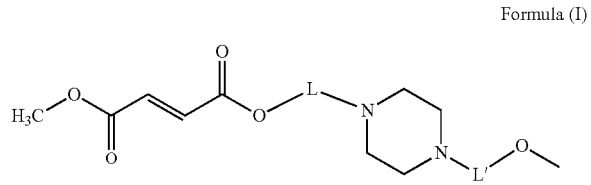

Formula (I)

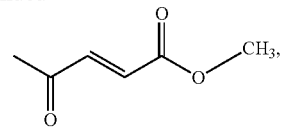

wherein L and L' are each an alkanediyl residue with 1 to 6 carbon atoms.

2. Compound according to claim 1, wherein L and L' are the same alkanediyl residue.

3. Compound according to claim 1, wherein L and L' are linear alkanediyl residues.

4. Compound according to claim 1 represented by Formula (Ia)

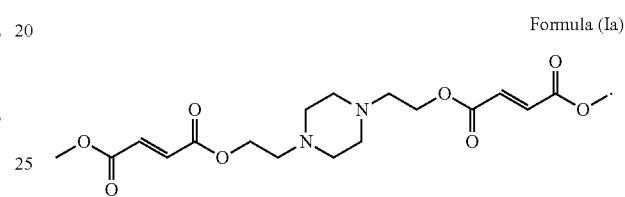

Formula (Ia)

5. Pharmaceutical composition comprising a compound according to claim 1.

6. Pharmaceutical composition, comprising (i) 0.01 to 10 mmol of a compound according to claim 1, and (ii) optionally, pharmaceutical excipients.

7. Pharmaceutical composition according to claim 5, wherein the composition is a solid oral dosage form.

8. Pharmaceutical composition according to claim 5, wherein the in-vitro drug release after 2 hours is less than 10%, measured according to USP, Apparatus II, paddle, 0.1N HCl, 37° C., 50 rpm.

9. A method for treating systemic diseases, autoimmune diseases and/or inflammatory diseases, comprising administering to a subject in need thereof a therapeutically effective amount of the compound according to claim 1.

10. The method of claim 9, wherein the autoimmune diseases are multiple sclerosis or psoriasis.

* * * * *